United States Patent [19]

Adams

[11] Patent Number: 4,727,277

[45] Date of Patent: Feb. 23, 1988

[54] ELECTRONIC BUBBLE DETECTOR APPARATUS

[76] Inventor: Tello Adams, 8400 141st St. North, Seminole, Fla. 33542

[21] Appl. No.: 1,901

[22] Filed: Jan. 9, 1987

[51] Int. Cl.$^4$ .............................. H01L 41/08
[52] U.S. Cl. ..................... 310/321; 310/323; 310/338; 310/324; 310/800; 310/316; 73/290 V
[58] Field of Search ............... 310/316, 317, 319, 321, 310/322, 323, 324, 338, 339, 800; 73/702, 704, 715, 754, 716, 717, 753, 290 V; 340/619–621; 324/61 P, 61 QS; 128/715

[56] References Cited

U.S. PATENT DOCUMENTS

| | | | |
|---|---|---|---|
| 3,603,152 | 9/1971 | Alibert | 310/338 X |
| 3,816,773 | 6/1974 | Baldwin et al. | 310/321 X |
| 3,879,992 | 4/1975 | Bartera | 310/321 X |
| 3,903,733 | 9/1975 | Murayama et al. | 310/800 X |
| 4,019,072 | 4/1977 | Mifune et al. | 310/338 X |
| 4,088,916 | 5/1978 | Weineck | 310/338 |
| 4,146,875 | 3/1979 | Beatson | 310/338 X |
| 4,176,524 | 12/1979 | Kamiyama | 310/324 X |
| 4,193,010 | 3/1980 | Kompanek | 310/324 X |
| 4,214,484 | 7/1980 | Abts | 310/338 X |
| 4,314,242 | 2/1982 | Kuru et al. | 310/321 X |
| 4,540,981 | 9/1985 | Lapetina | 310/321 X |
| 4,600,855 | 7/1986 | Strachan | 310/323 X |

*Primary Examiner*—Mark O. Budd

[57] ABSTRACT

An oscillator utilizes a piezo-electric transducer as a frequency determining element. The transducer, when unloaded, has a resonant frequency which determines the oscillation frequency and exhibits a predetermined level of amplitude excursion. The transducer, when moved into engagement with a conduit through which fluid flows, becomes loaded and exhibits a change of resonant frequency, whereby the oscillator frequency changes, and also exhibits a change in level of amplitude excursion. The amount of oscillator frequency change and the change in excursion level have respective values when the fluid flowing in the conduit past the transducer is bubble free which differ from the respective values when the fluid contains bubbles. Circuitry responsive to at least one of the changing frequency and amplitude values produces a signal when a selected one of the bubble free and bubble containing conditions is detected.

8 Claims, 3 Drawing Figures

ELECTRONIC BUBBLE DETECTOR APPARATUS

BACKGROUND OF THE INVENTION

It is often necessary as for example in air conditioning and heating systems to eliminate or prevent the formation of bubbles such as gas bubbles in fluids flowing through pipes and other conduits. Accordingly visual displays such as signt glasses are employed to enable fluid flow to be monitored. However, depending upon the type of fluid and type of conduit, such displays cannot be or are not always used. Moreover, even when such displays are used, periodic visual inspection by trained observers is necessary, and, even under these conditions, dangerous bubble conditions can develop between inspection periods and thus be undetected. The present invention is directed toward electronic apparatus which will automatically and continuously detect the presence or absence of bubbles in fluid flows and which will produce an electrical signal which can be used to sound an alarm, operate control devices or initiate other immediate corrective action. Since the apparatus, once installed, can be operated remotely, it can be used in radioactive and other environments in which operator access is dangerous or forbidden.

SUMMARY OF THE INVENTION

In accordance with the principles of the invention, electronic apparatus is adapted for use with any conduit through which fluid flows to determine whether or not bubbles are present in the fluid.

The apparatus utilizes an oscillator which employs a piezo-electric transducer as a frequency determining element. The transducer, when free of any load, has a resonant frequency which determines the oscillator frequency, and also exhibits a pretermined level of amplitude excursion. When the transducer is placed in engagement with the outer surface of the conduit, the mass flow of the fluid past the transducer crets a load thereon. Consequently, the resonant frequency of the transducer changes as does its level of amplitude excursion. The amount of oscillator frequency change and the amount of change in excursion level have respective values when the fluid flow past the transduceris bubble free which differ from the respective values when this fluid flow contains bubbles.

Means responsive to the changing values of frequency or amplitude level produces a signal when bubble containing flow is present, or, alternatively, when the flow is bubble free. The signal can be used to produce a visual and/or audible signal to produce an alarm, operate control devices, or otherwise initiate appropriate corrective action.

The foregoing and other objects and advantages of this invention as well as other objects and advantages thereof will either be explained or will become apparent to those skilled in the art when this specification is studied in conjunction with the accompanying drawings and specific description of preferred embodiments which follow.

DETAILED DESCRIPTION OF PREFERRED EMBODIMENTS

Figures 1, 2:
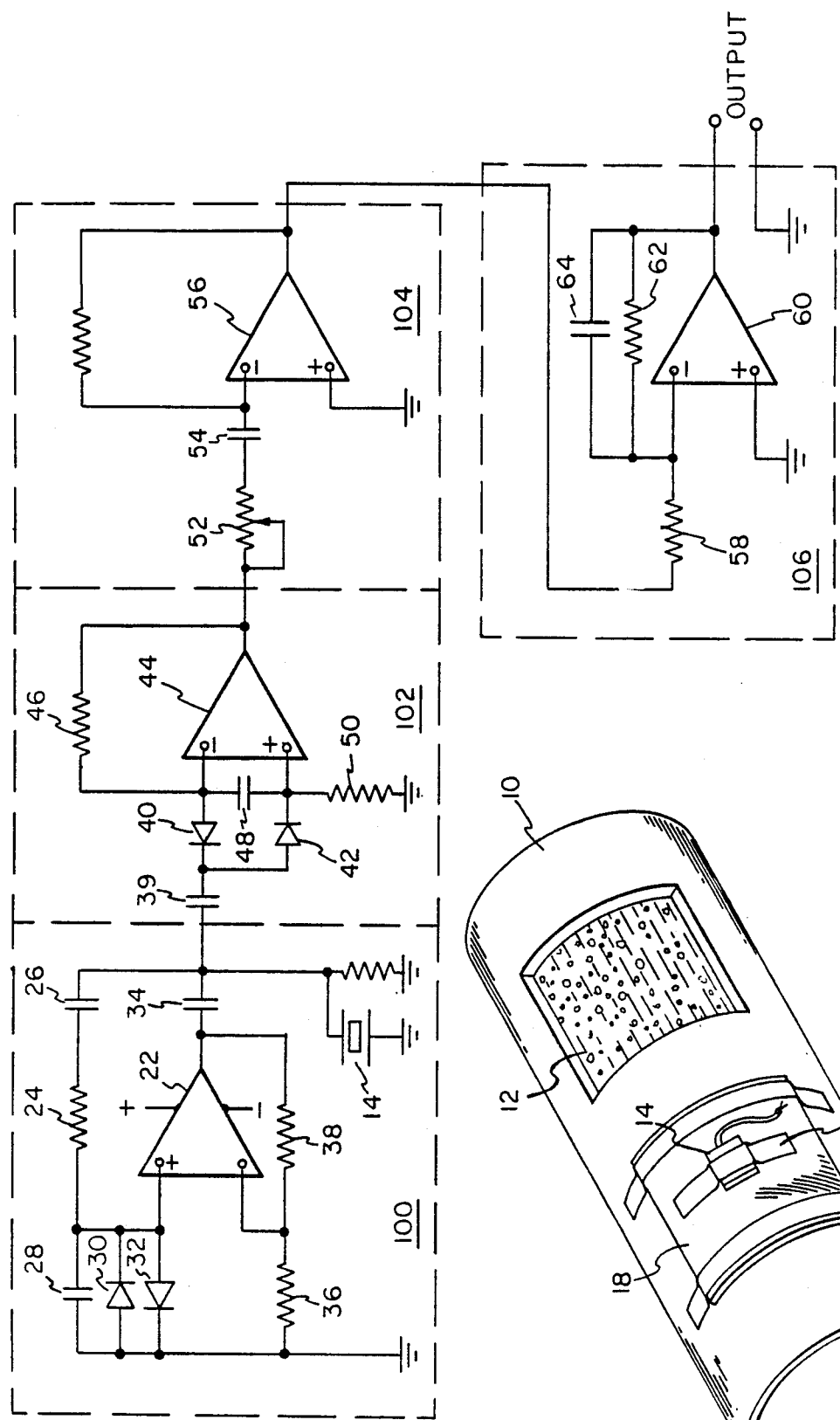
FIG. 1 is a perspective view of a piezo-electric transducer engaging the outer surface of a pipe in accordance with the invention.
FIG. 2 illustrates one embodiment of a circuit which responds to changes in the level of amplitude excursion and which can be used with the structure shown in FIG. 1.

Referring first to FIG. 1, there is shown a conduit or pipe 10 through which a fluid 12 flows, a portion of the fluid containing bubbles. A piezo-electric ceramic transducer 14 is secured to the outside of the pipe, as for example, by masking tape 16, with a thin layer 18 of neoprene disposed between the transducer and the outer surface of the pipe. This arrangement is used to insure good area engagement between the transducer and the pipe regardless of irregularities in the pipe surface. The transducer can be a thin flat disc having, for example, a diameter of 0.25 inches and a thickness of 0.08 inches. The flat surface of the disc is engaged via the layer 18 with the pipe surface. When the outer surface of the pipe is smooth without recesses or bumps, layer 18 need not be used.

Transducers, depending upon their geometry, have resonant frequencies which differ, depending upon the mode of operation. Transducer 14 can resonate in the radial mode, across the disc, whereby the amplitude excursions of the disc cause it to elongate and contract in the plane of the disc, and can also resonate in the axial mode, through the disc, whereby the amplitude excursions of the disc cause it to elongate and contract in a direction perpendicular to the plane of the disc. The radial mode amplitude excursions were found to be sufficient for use with the circuit shown in FIG. 2. The particular transducer described above was found to have a resonant frequency [unloaded] of about 320 kilohertz.

Referring now to FIG. 2, an oscillator 100 using transducer 14 yields a first signal. The first signal is at carrier frequency [the oscillator frequency] which in the presence of bubbles in the fluid flow is amplitude modulated by the amplitude excursions of the loaded transducer. This first signal is supplied to the input of a signal detector and low pass filter stage 102. Stage 102 removes most of the carrier frequency component from the first signal and derives therefrom a second signal. The second signal consists primarily of an alternating current component, the frequency and amplitude of which is proportional to the amplitude excursions of the transducer caused by the presence of bubbles, superimposed on a direct current component representing the amplitude excursions of the transducer caused by an undisturbed fluid flow. The second signal also contains a small unwanted carrier frequency component, since the stage 102 removes most but not all of this component. The second signal is supplied to the input of stage 104 which is a high pass filter with gain. Stage 104 removes the direct current component from the second signal and derives therefrom a third signal which contains the alternating current component and the unwanted carrier frequency component. The third signal is supplied to the input of stage 106 which is a low pass filter with gain. Stage 106 removes the unwanted carrier frequency component from the third signal and derives therefrom a fourth signal which contains only the alternating current component and thus identifies uniquely the presence of bubbles in the fluid. When the fourth signal has a zero value, this zero value identifies uniquely the absence of bubbles in the fluid.

The oscillator stage 100 employs an operational amplifier 22 with a positive feedback loop including a high pass filter formed by capacitor 26 and resistor 24 and a low pass filter formed by resistor 24 and capacitor 28. These filters are in series, the bottom frequency of the high pass filter being essentially the same as the top frequency of the low pass filter. These frequencies are essentially the same as the resonant frequency of the transducer and prevent oscillation in undesired modes. Diodes 30 and 32 set the range of the amplitude of the oscillations and the range of the amplitude excursion of the transducer. Capacitor 34 determines the drive level to the transducer, and, to some extent. the phase, while resistors 36 and 38 control the maximum loops gain.

The first signal is supplied via capacitor 39 to the next stage. The detector action is provided by diodes 40 and 42 and operational amplifier 44. Resistors 46 and 50 and capacitor 48 constitute a low pass filter.

The second signal appears at the output of amplifier 44 and is supplied via high pass filter [gain control rheostat 52 and capacitor 54] to operational amplifier 56. The third signal appears at the output of amplifier 56 and passes through resistor 58 to the input of another operational amplifier 60. The feedback loop between the output and one input of amplifier 60, includes a low pass filter defined by resistors 62, 58 and shunting capacitor 64. The desired fourth signal appears at the output of amplifier 60. Thus the arrangement of FIG. 2 utilizes the change in amplitude excursion of the transducer to produce the fourth signal.

Figure 3:
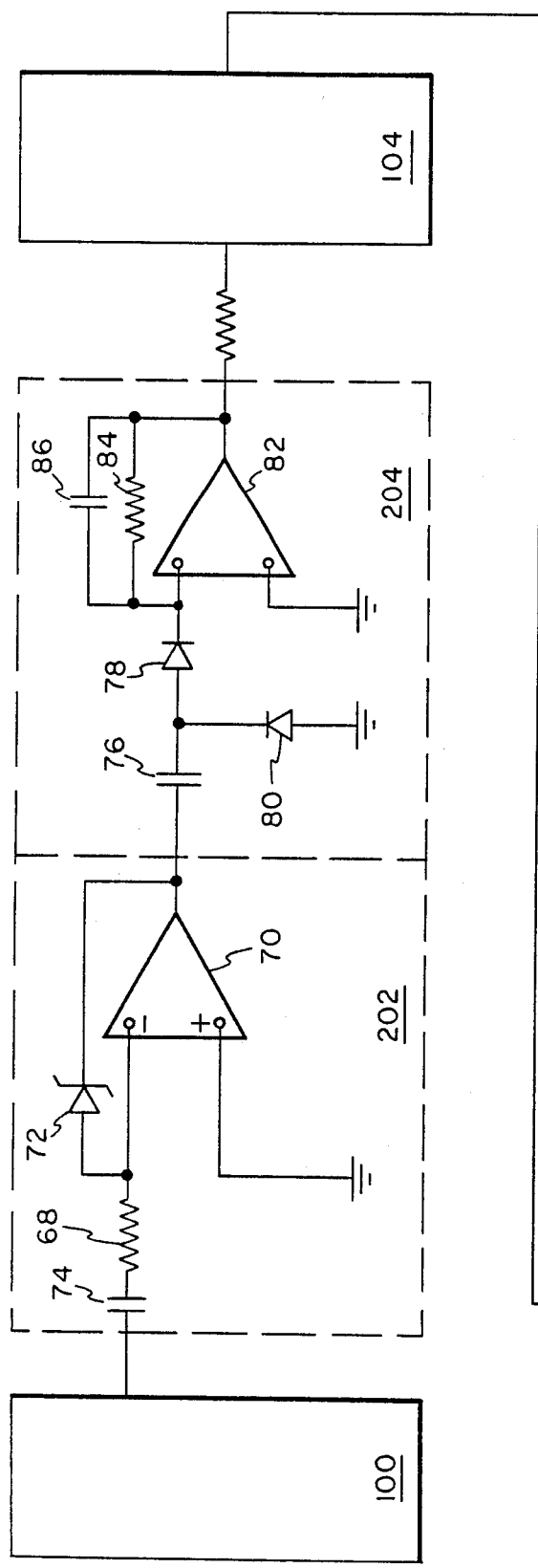
FIG. 3 illustrates an embodiment of a circuit which responds to changes in frequency and which can be used with the structure shown in FIG. 1.
Figure 3:
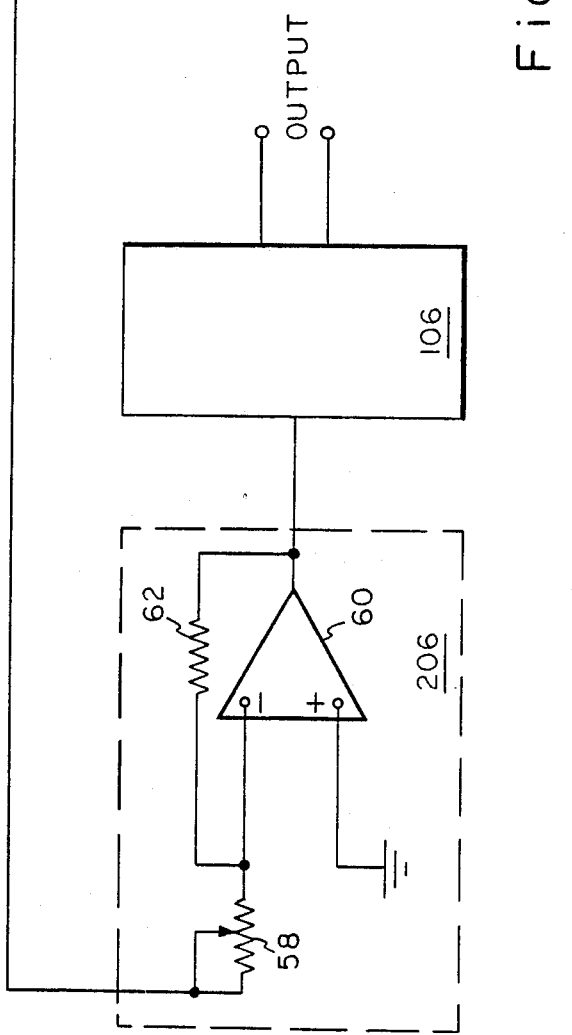

Referring now to FIG. 3, the same first signal appears at the output of the same stage 100 as in FIG. 2. However, the arrangement of FIG. 3 utilizes the change in frequency rather than the change in amplitude excursion. To this end, the first signal is supplied to a second stage 202 which derives from the first signal a square wave signal of fixed amplitude. This square wave signal is supplied to a third stage 204, which converts the square wave signal to a signal substantially identical in wave form to the second signal obtained from stage 102. This substantially identical signal is then supplied through stage 104 and then through stage 106 in the same manner as in FIG. 2. However, unlike the arrangement in FIG. 2, an amplifier stage 206 is inserted between stages 104 and 106 to provide additional gain because the desired fourth signal yielded at the output of stage 106 of FIG. 3 would otherwise be at too low a level as compared to the fourth signal yielded at the output of stage 106 in FIG. 2.

Stage 202 consists of capacitor 74, resistor 68, operational amplifier 70 and zener diode 72 connected between the output and one input of amplifier 70.

Stage 204 consists of capacitor 76, diodes 78 and 80, operational amplifier 82 and a low pass filter [resistor 84 and shunting capacitor 86] connected between the output and input of amplifier 82.

Stage 206 is substantially identical to stage 106 except that stage 206 does not use capacitor 64. The elimination of this capacitor eliminates the use of a low pass filter which, in this stage, is undesired.

All of the operational amplifiers can be identical, but have been given different identification numbers to facilitate the description of the circuitry.

While the fundamental novel features of the invention has been described and pointed out, it will be understood that various substitutions and changes in the form of the details of the embodiments shown may be made by those skilled in the art without departing from the concepts of the invention as limited only by the scope of the claims which follow.

What is claimed is:

1. Electronic apparatus adapted for use with a conduit through which a fluid flows, the fluid having a first bubble free state and a second and alternative bubble containing state, said apparatus comprising:

an oscillator employing a single piezo-electric transducer as a frequency determining element, the transducer having different frequency modes of operation enabling the transducer to resonate at different frequencies, the oscillator having a positive feedback loop containing in series a high pass filter and a low pass filter which together determine one selected mode of operation and eliminate any other transducer frequency mode, the transducer, when unloaded and operating in the selected mode, having a resonant frequency which determines the oscillation frequency and having a predetermined maximum level of amplitude excursion, the transducer, when loaded by being moved into engagement with the conduit, exhibiting a change in resonant frequency and a change in the level of amplitude excursion while remaining in the selected mode, the amount of oscillator frequency change and the amount of change in excursion level having respective values when the fluid is in the first state which differ from the respective values when the fluid is in the second state; and means responsive to at least one of the changing frequency and amplitude values to produce a signal when a selected one of the states is detected.

2. Electronic apparatus adapted for use with a conduit through which a fluid flows, the fluid having a first bubble free state and an second and alternate bubble containing state, said apparatus comprising:

an oscillator employing a flat piezo-electric transducer as a frequency determining element, the transducer having axial and radial modes of excitation which have different resonant frequencies, the oscillator having a positive feedback loop containing in series a high pass filter and a low pass filter which together determine one selected radial mode of excitation for the transducer together with an associated resonant frequency and prevent the transducer from being excited in an axial mode of excitation, the transducer, when unloaded and operating in the selected radial mode wherein its amplitude elongations and contractions take place in the plane of the transducer, having a resonant frequency which determines the oscillation frequency and having a predetermined maximum level of amplitude excursion, the transducer, when loaded by being moved until one flat surface of the transducer is in engagement with the conduit, exhibiting a change in resonant frequency and a change in the level of amplitude excursion while remaining in the selected radial mode, the amount of oscillator frequency change and the amount of change in excursion level having respective values when the fluid is in the first state which differ from the respective values when the fluid is in the second state; and means responsive to at least one of the changing frequency and amplitude values to produce a signal when a selected one of the states is detected.

3. Apparatus as set forth in claim 2 further including additional means to secure the transducer to the outside of the conduit in such manner that one flat surface of the transducer is in engagement with the conduit.

4. Apparatus of claim 2 wherein the means responds to the changing frequency values.

5. Apparatus of claim 2 wherein the means responds to the changing amplitude values.

6. Apparatus of claim 2 wherein the oscillator is provided with excursion limiting means to set said predetermined level of amplitude excursion.

7. Apparatus of claim 2 wherein the transducer is a disc.

8. Apparatus of claim 6 wherein the excursion limiting means includes a pair of diodes.

* * * * *